(12) United States Patent
Livolsi (10) Patent No.: US 7,125,251 B2
(45) Date of Patent: Oct. 24, 2006

(54) ADJUSTABLE IMPRESSION TRAY WITH VARIABLE GEOMETRY

(76) Inventor: Lydie Livolsi, 171 Rue de Cernay S1100, Reims (FR)

( * ) Notice: Subject to any disclaimer, the term of this patent is extended or adjusted under 35 U.S.C. 154(b) by 0 days.

(21) Appl. No.: 10/511,180

(22) PCT Filed: Apr. 15, 2003

(86) PCT No.: PCT/FR03/01199

§ 371 (c)(1),
(2), (4) Date: Oct. 14, 2004

(87) PCT Pub. No.: WO03/086226

PCT Pub. Date: Oct. 23, 2003

(65) Prior Publication Data

US 2005/0153256 A1  Jul. 14, 2005

(30) Foreign Application Priority Data

Apr. 15, 2002 (FR) .................................. 02 04699

(51) Int. Cl.
*A61C 9/00* (2006.01)
(52) U.S. Cl. ....................................................... 433/41
(58) Field of Classification Search ................. 433/37, 433/39, 41–43, 45, 46, 48, 34, 47, 38, 71; 128/859, 861, 862; 249/155
See application file for complete search history.

(56) References Cited

U.S. PATENT DOCUMENTS

| | | | | |
|---|---|---|---|---|
| 347,976 A | * | 8/1886 | Starr | ............................ 433/41 |
| 3,990,151 A | * | 11/1976 | Kesling | ......................... 433/23 |
| 4,145,812 A | | 3/1979 | Johnson | |
| 4,401,616 A | | 8/1983 | Wagner | |
| 5,340,308 A | | 8/1994 | Cukjati | |
| 5,752,826 A | * | 5/1998 | Andreiko | ...................... 433/41 |
| 6,213,768 B1 | * | 4/2001 | Wright | .......................... 433/37 |
| 6,428,315 B1 | * | 8/2002 | Prestipino et al. | ............. 433/45 |

FOREIGN PATENT DOCUMENTS

| | | |
|---|---|---|
| DE | 331 935 C | 1/1921 |
| EP | 0074182 | 3/1983 |
| FR | 1 541 691 A | 10/1968 |
| FR | 2 186 829 A | 1/1974 |
| FR | 2 551 654 | 9/1983 |
| WO | WO 00/09032 | 2/2000 |

* cited by examiner

Primary Examiner—Todd E. Manahan
Assistant Examiner—Meoghan E. MacPherson
(74) Attorney, Agent, or Firm—Davis & Bujold, P.L.L.C.

(57) ABSTRACT

The invention relates to an adjustable impression tray (1) comprising a trough (2) in the form of an arch with a straight central portion (7) extended by two lateral branches (8,9), essentially matching the form of a dental arch and comprising several integral zones which may be deformed at the temperature of use in the form of a multi-directional extension means (12), for example an accordion-like bellows arrangement (13 to 16). The impression tray, preferably for single usage, advantageously comprises splitting zones (17, 18) which allow the production of impression trays of differing sectors, which by comprising one or several deformation zones are equally adjustable. The invention is of interest to dentists and prosthetic dentists and more generally to producers and users of dental equipment.

21 Claims, 7 Drawing Sheets

ADJUSTABLE IMPRESSION TRAY WITH VARIABLE GEOMETRY

This application is a National Stage completion of PCT/FR2003/001199 filed Apr. 15, 2003, which in turn claims priority from French Patent Application Ser. No. 02/04699 filed Apr. 15, 2002.

FIELD OF INVENTION

The present invention relates to a dental impression tray of adjustable size intended mainly for dentistry.

TECHNOLOGICAL BACKGROUND TO THE INVENTION

In the field of dentistry, it is often necessary to manufacture and install prostheses. These refer to bridges and, dental apparatuses of various types or similar. Prior to the manufacture of these prostheses, it is essential to take an impression of the denture of the patient. This impression makes it possible to subsequently manufacture a dental prosthesis with specific measurements in a laboratory.

For this purpose, the expert uses a device called an impression tray. This is made of a gutter approximately in the shape of a horseshoe and which matches the shape of a dental arch. The dentist fills this gutter with a pasty substance for impression taking. The impression tray is then introduced into the mouth of the patient. The patient bites the paste to leave an impression of the trace of his or her teeth.

To ensure that the impression is usable, all teeth must be correctly pressed into the paste. It is obvious that the dimensions of the impression tray are decisive. They must be adapted to the morphology of the dental arches of the patient.

In order to be able to adapt to the many morphologies in various patients, experts are currently obliged to possess a wide range of impression trays in various sizes. In each case, they must choose the model to be used.

The aim of the invention is to provide a universal impression tray which may be adapted to all dentures.

This universal impression tray must be able to be easily and quickly adapted to all sizes of dentures. This process should not require a specific resource or a specific particular substance, in addition to those constituting the impression tray.

In addition, this impression tray must be easy and inexpensive to manufacture. It must also be simple, rapid and practical to use.

Moreover, it is advantageous that this impression tray can be used in several parts in order to obtain a sectoral impression tray intended for one section of the denture of the patient only.

To solve this technical problem, several previous devices existed in former dentistry.

To adapt to the morphology of the denture of the patient, one of the former techniques involved adjusting the dimensions of an adaptable impression tray to the size of the denture of the patient prior to taking the impression. Another technique consisted in assembling an impression tray comprising several elements so as to be adapted to the size of denture.

With regard to the formation of a sectoral impression tray, the solution usually used involves assembling elements forming the segment side of the impression tray (U.S. Pat. No. 4,145,812 in the name of JAMES F JOHNSON) or using dividable lines in a traditional impression tray of fixed size made of plastic. However, these solutions are seldom compatible with the former techniques allowing for adaptation of the size of the impression tray.

According to the first technique, we could take, for example, the device described in PCT disclosure No. WO 00/09032 published in the name of INTERNATIONAL DENTSPLY Inc. This is a malleable impression tray whose form is adaptable during a preliminary adjustment process. This preliminary process consists of heating the impression tray, which is made of a thermoformable material, stretching it and modelling it in a suitable way. This process then involves cooling the thermoformable material to obtain solidification in the desired configuration. This solidarisation is carried out before filling the impression tray of paste and carrying out the impression-take.

The European patent application No. EP 0074182 published in the name of WAGNER, mentioned a dental impression tray formed by heating deformable thermoplastic material sheet. The conformation of this sheet is carried out on a test model of the edge of the jaw of the patient, followed by cooling in a mainly rigid state.

These two devices cannot be used directly. They require preliminary working according to a long and difficult to apply process. This process requires the use of expensive additional and specific equipment. These devices thus are not suitable for the technical problem raised. They only allow for limited adaptation to varying morphologies. Moreover, they do not allow for the creation of a sectoral impression tray.

The second method of adaptation is illustrated, for example, by the French patent application No. FR 2551654 by DECROB LOUIS. This application describes an adjustable metal impression tray using a bolt or a central rivet. This bolt or rivet will allow for the articulation of the gutter of the impression tray, in two symmetrical parts, using the level of a clevis pin.

Another example is disclosed in the U.S. Pat. No. 5,340,308 issued in the name of JOSEPH F CUKJATI. This patent describes an impression tray made up of several elements assembled in an adjustable way to the size of denture of the patient.

Nevertheless, devices of this type are expensive and not very practical. They must be assembled and mounted using tools before being able to be used. They cannot generally apply to all sizes of denture. They are, moreover, difficult to clean. In addition, they are not designed to be split for sectoral impression trays.

On the contrary, the impression tray described in the invention makes it possible to solve this technical problem in a particularly simple, fast, practical and inexpensive way.

SUMMARY OF THE INVENTION

The device according to the invention is a dental impression tray for the taking of a sectoral or full impression of the upper or lower jaw. This impression tray is made up of a gutter in the general shape of an arch with a central curved section extended on both sides by two lateral branches. This gutter is made up of a basic wall bordered longitudinally by two side walls, one interior and the other exterior. These side walls create a receiving groove which may be filled with paste for impression-taking. A specific characteristic of this impression tray is that the gutter presents at least one integrated zone which is subject to multidirectional extension at the temperatures used.

At least one of these zones of multidirectional extension will preferably include an unfolding structure.

This unfolding structure has the advantage of being bellows, and preferably bellows of the accordion type.

According to the preferred mode of application of the invention, the impression tray comprises four zones of multidirectional extension. Two of these zones of extension, are located, for example, on the central curved section of the gutter and are placed mainly at the ends of the gutter. One zone of extension, for example, is envisaged on each side branch of the gutter.

These zones of multidirectional extension make it possible to widen or tighten the impression tray, to lengthen or shorten the side branches of the gutter, or also to modify the slope of these side branches. It is thus possible, according to the description of the invention, to adapt the impression tray easily and quickly to all sizes of denture, simply by actuating the various concertina covers on the tray.

According to the description, the impression tray can be made out of conventional plastic allowing for pressurized sterilization and therefore re-use.

However, the tray should preferably be manufactured in disposable plastic and for single use. The tiresome stages, prior to impression-taking, cleaning and sterilization of the impression tray are thus avoided for the dentist, who will save invaluable time.

According to the description, the impression tray has the advantage of being capable of including at least one dividable zone with lower mechanical resistance. This dividable zone box makes it possible to split the impression tray into one or more sectoral impression trays.

The sectoral impression trays created will preferably include one or more integrated zones which deform at temperatures used in the form of one or more zones of multidirectional extension. This or these deformable zone(s) is or are, preferably one or more concertina covers. This makes size regulation possible. The storage of multiple sectoral impression trays of different sizes by the dentists is also therefore of no utility.

BRIEF DESCRIPTION OF THE DRAWINGS

Other characteristics and advantages of the invention will appear with the reading of the detailed description which will follow, description made in reference to the annexed drawings, in which.

DETAILED DESCRIPTION OF PREFERED EMBODIMENTS

The adjustable impression tray according to the present invention will now be described in a detailed way with reference to FIGS. 1 to 17. The numbered elements provided on the various Figures will be used within the following description.

In the continuation of this description, one part will describe the "top impression tray" the impression tray intended to capture the impression of a superior dental arch. One part will describe the "bottom impression tray" the impression tray intended to capture the impression of an inferior dental arch.

In the same way, the concepts of a top or a lower face, a top part or lower part, etc. concerning the impression tray of this invention will be defined and compared to the following orientation. The defined orientation of the impression tray is when it is positioned in the mouth of the patient ready to carry out an impression.

In the various Figures, the impression trays represented correspond to preferred configurations and embodiments of the invention that will be described in detail thereafter.

It must however be understood that they are only some examples of the many configurations possible of the invention. The one skilled in the art can make modifications without leaving the framework of this invention.

Figure 1:
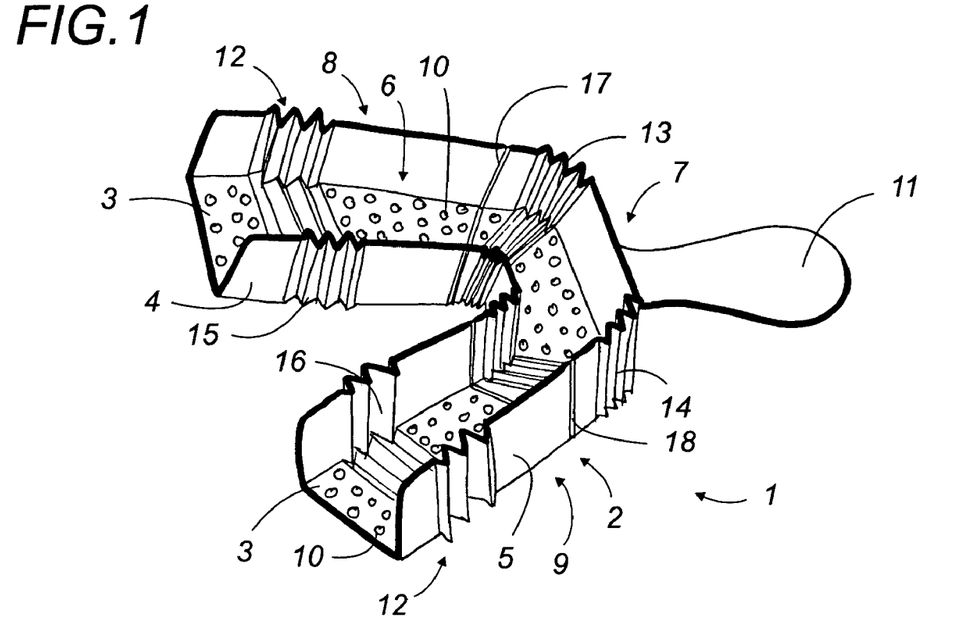
FIG. 1 is a top perspective view of an impression tray according to the invention for a lower dental arch.
Figure 3:
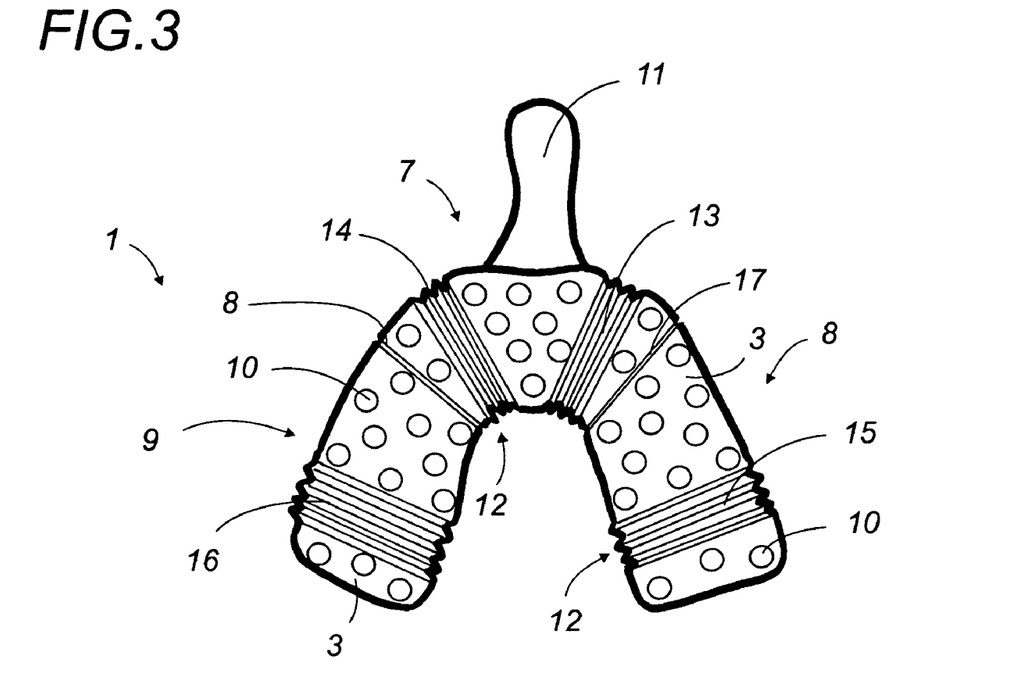
FIG. 3 is a plan view of the top face of an impression tray according to the invention of the lower dental arch.

FIGS. 1 and 3, represent an impression tray bottom 1 according to the invention.

In a traditional way, this impression tray bottom 1 is composed mainly of a gutter 2 appreciably in the shape of an arch or horseshoe so that it is able to match the shape of a lower dental arch.

Gutter 2 is made from two sidewalls either side of the base 3 that is basically horizontal. These two sidewalls, interior 4 and external 5 border the base 3 longitudinally. These sidewalls are preferably approaching vertical, thus defining a receiving throat 6 being able to be filled with paste to capture the impression.

Gutter 2 includes a central curved section 7 elongated on both ends by two side branches 8 and 9.

In order to improve adhesion of the paste used to capture the impression in the impression tray, the base 3 comprises for example multiple perforations 10. The sidewalls 4 and 5 can also be provided with multiple perforations 10. These perforations also allow the escape of excess paste during capture of the impression when the patient bites onto the impression tray forming an impression of their teeth. Under the pressure exerted by the patient, the surplus paste can escape out of the impression tray through these perforations. The formation of bubbles is also avoided.

Perforations 10 are for example of circular form. They can be identical or of various shapes within the same impression tray. These perforations 10 can obviously remain unspecified and be different from those represented on the Figures. The one skilled in the art can choose their form, their number and their provision in a suitable way.

The adhesion of the paste within the impression tray can also be improved by the presence of relief's not illustrated, on the contact surfaces of the walls of the impression tray.

Additionally, in a preferential way, internal surfaces of the impression tray can be coated with an adhesive. Alternatively the contact surfaces of the walls of the impression tray can be provided with protuberances. The paste material of the impression thus forms an improved bond with the bottom and the side faces of the impression tray.

In order to allow the expert and more generally the user to hold and handle the impression tray easily, it preferably comprises a gripping stem or leg 11.

This stem or leg 11 can be interdependent of impression tray 1. It can also form an integral part of the impression tray. It can also be an independent part having to be assembled onto the impression tray. This part could also be plugged into the impression tray or be bonded onto the impression tray before its use. The complementary method of fixing can be achieved by matching profiles or shapes of the stem 11 and the impression tray 1. These means, known to the one skilled in the art, will not be described further.

According to an essential feature of the invention, the impression tray of bottom 1 provides at least one deformable zone 12 integrated into the gutter 2 that can be modified at ambient temperature. This zone is for example in the form of a means of simple or multidirectional extension. The preferred embodiment represented comprises four of them. They are for example four convoluted bellows of the accordion type.

Two means of multidirectional extension for example are 13 and 14, located on the ends of the central curved section 7 of gutter 2. They are located, for example in the same orientation and at the ends of gutter 2 in the section of curve in the gutter forming an arch or horseshoe. They are two of the bellows envisaged above. The two other bellows, 15 and 16, are respectively positioned on the side branches 8 and 9, preferably in the same orientation and positioned towards the free ends away from the curved section 7.

These bellows, formed comparable to those of an accordion comprise of folds and successive folds of similar dimensions in opposite directions, providing a means of lengthening and a multiplicity of angular orientations of the branches of the impression tray in the same plane. The various modifications and possible adaptations provided by these bellows will be explained in the continuation of this description by reference to the diagrammatic FIGS. 5 to 9.

Advantageously, these bellows, form zones in relief and hollow in the walls of the impression tray. These reinforce further the adhesion of the paste used to capture the impression within the gutter 2.

These bellows can be perforated in a particular way or a different way or a similar way to the remainder of the impression tray.

Preferentially, the impression tray of bottom 1 according to the invention can additionally provide one or more split lines of lower mechanical strength. The alternative represented comprises two of these split lines, referenced 17 and 18.

These split lines correspond to a localized thinning or a weakening, for example in the form of a precut, in the material from which the impression tray is constructed. The pactitioner or the user can thus divide the impression tray utilizing these split lines. The practitioner can split the impression tray into one or more impression trays such as sections 19.

The split lines 17 and 18 of the preferred embodiment represented are located approximately at the junction between the central curved section 7 and the side branches 8 and 9 of the gutter. They are located, preferably and respectively between bellows 13 and 15, and 14 and 16.

One obtains, after rupture of these split lines three impression trays sections 19. They are a curved impression tray 20 and two side trays, respectively 21 and 22. They are represented split apart on FIG. 9. The two side impression trays sections 21 and 22 are preferably symmetrical.

Figure 9:
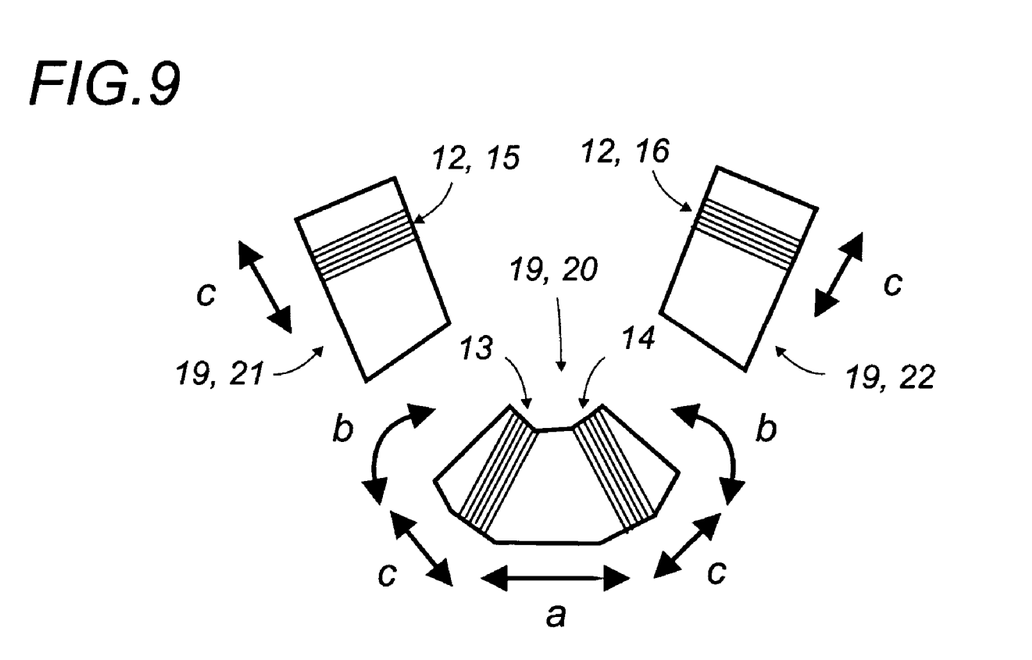
FIG. 9 is a diagrammatic view of the top face of different sectoral impression trays which may be obtained from the under impression tray according to the invention shown on FIG. 3, the various adaptability of these sectoral impression being symbolized by arrows.

Advantageously in this preferred embodiment an oral impression tray section 19 comprises at least one means of multidirectional extension 12. This means is preferably again bellows of the accordion type. This makes it possible to individually regulate their size and/or their angle in order to enable them to be adapted to a broad range of dentures.

Figure 2:
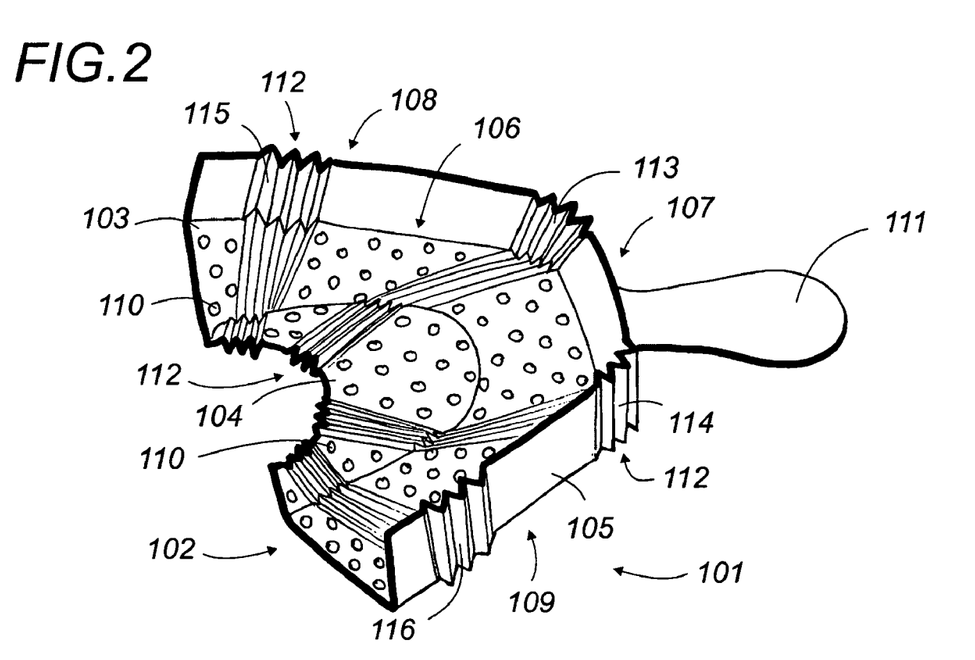
FIG. 2 is a top perspective view of an impression tray according to the invention of the superior dental arch.
Figure 4:
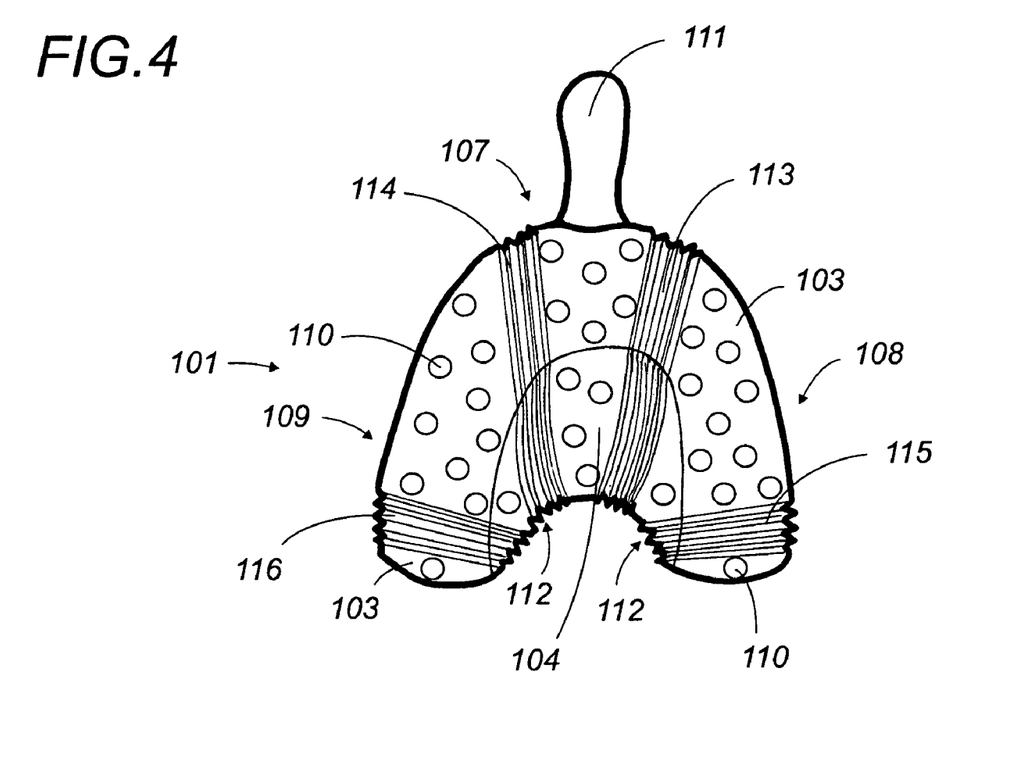
FIG. 4 is a plan view of the lower face of an impression tray according to the invention of the superior dental arch.

On FIGS. 2 and 4, the embodiment represented this time is an impression tray top 101 according to the invention. This embodiment has a structure largely similar to that of the impression tray bottom 1 previously described.

It is composed of a gutter 102 appreciably in the shape of arch or horseshoe. It is likely to match the shape of a higher dental arch. It is made of an appreciably horizontal lower base 103, bordered longitudinally by two sidewalls, interior 104 and external 105. They define a receiving throat 106 thus being able to be filled with a paste to capture an impression.

Gutter 102 of the impression tray top 101 is made up of a central part 107 in curved section. This gutter 102 is extended on both sides by two side branches 108 and 109.

As previously, the external sidewall 105 rises appreciably vertically. However, the interior sidewall 104 is formed differently. Indeed, this wall 104 widens and a part rises centrally and higher to form a raised plateau in the form of a vault. This embodiment is intended to match the shape of the roof of the mouth. The impression tray top 101 provides the means to take an impression of the velum in addition to that of the higher dental arch.

The impression tray top 101 can also be provided with multiple perforations 110. These exist in particular on its base 103 and/or its sidewalls 104 and 105.

Preferably, the impression tray top 101 also comprises a gripping handle 111. This gripping handle 111 can be formed out of a part of the tray or be reattached when required for use.

According to an essential feature of the invention, the impression tray top 101 presents also at least one multidirectional deformable extension zone 112 forming part of the impression tray top 101 that can be modified at ambient temperature. The preferred embodiment represented comprises four such zones, making it possible to adapt the impression tray to any anatomical shape encountered. These zones are four bellows of the accordion type.

Preferably, two of these bellows, 113 and 114, are located on the central part 107 appreciably at the ends of the central curved part 107. The two other bellows, 115 and 116, are respectively positioned on the side branches 108 and 109.

The means of extension, preferentially here bellows 113 to 116, are elongated on the interior side of the vault 104. An adjustment of impression tray 101 and the raised vault section 104 is thus also possible. This adjustment allows a perfect adaptation to the anatomical form of the patient, including the roof of the mouth.

Figure 5:
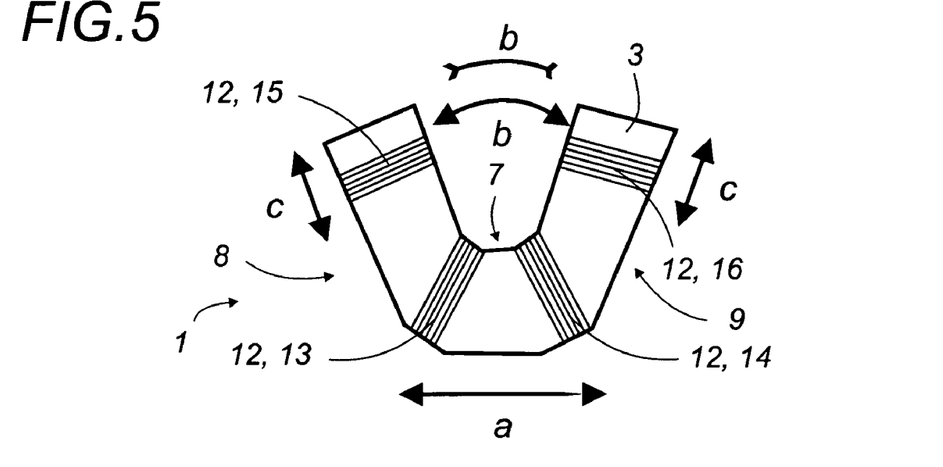
FIG. 5 is a diagrammatic view of the top face of the under impression tray shown on FIG. 3, the various adaptability being symbolized by arrows "a", "b" and "c"
Figure 6:
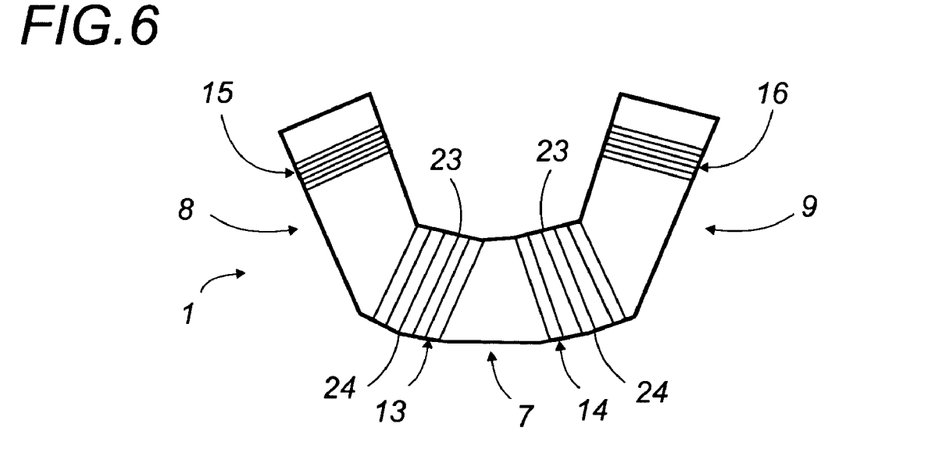
FIG. 6 is a diagrammatic view of the top face of the under impression tray shown on FIG. 5, stretched according to the arrow "a"
Figure 7:
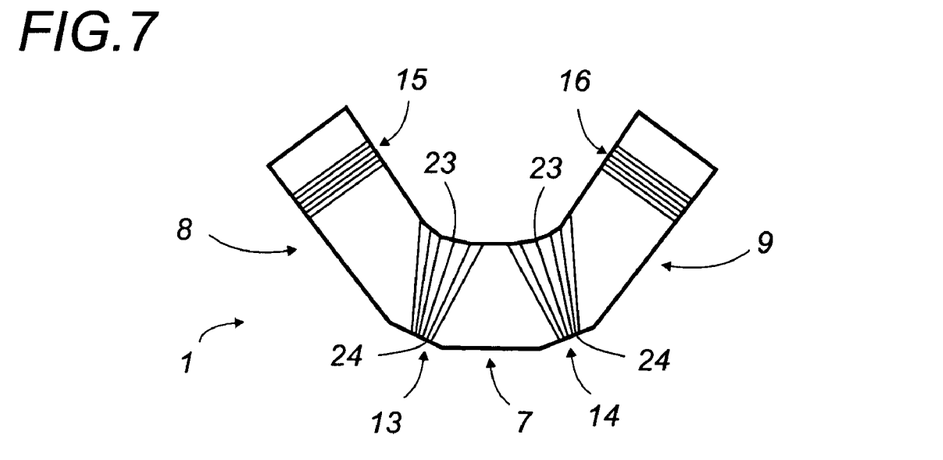
FIG. 7 is a diagrammatic view of the top face of the under impression tray represented on FIG. 5, stretched according to the arrow "b"
Figure 8:
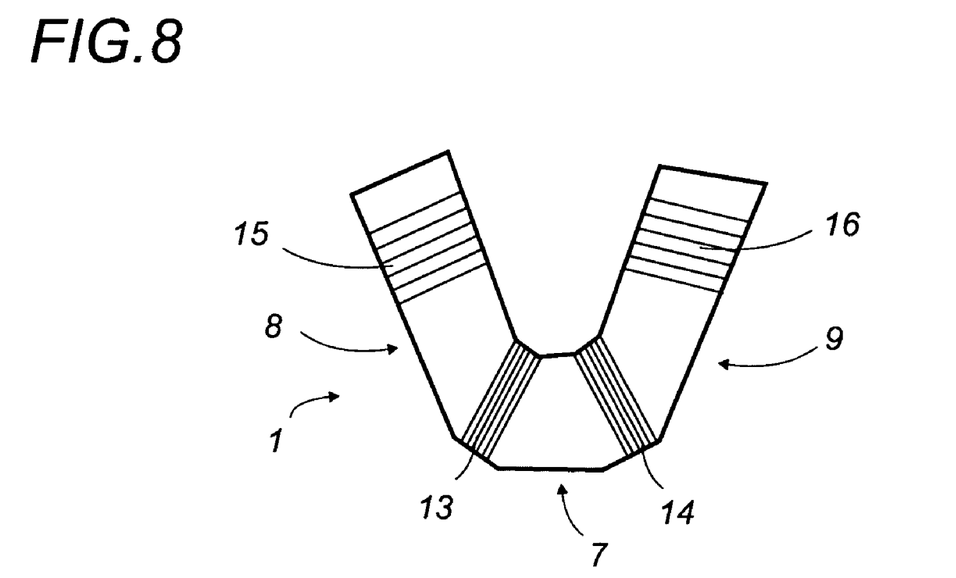
FIG. 8 is a diagrammatic view of the top face of the under impression tray shown on FIG. 5, stretched according to the arrow "c"

Arrows on FIG. 5 indicate the various adaptations of the impression tray according to the invention. The initial impression tray in FIG. 5 is then represented in FIGS. 6 to 8 showing some of the various stretched states that can be achieved. These diagrammatic states all originate from the impression tray bottom 1. It must however be understood that the same adaptability exists with the impression tray top 101.

Owing to the presence and to the position of the four deformable zones 12, preferably the four concertina sections 13 to 16, three types of elementary adjustment, symbolized by the arrows "a", "b" and "c", are possible.

The impression tray can be widened or tightened according to the arrow "a", by stretching or by compressing one or both central bellows 13 and 14. One can thus modify the length of the central curved section 7. Impression tray 1 is shown represented in FIG. 6 in a widened configuration.

The slope of the side branches, respectively 8 and 9, compared to the central section 7 can also be modified according to arrows "b". This angle modification is carried out while stretching or by compressing only one of the sides, interior 23 or outside 24, of the central bellows, respectively 13 and 14. FIG. 7 represents for example a configuration of the impression tray in which the angle of the side branches 8 and 9 have been increased and the distance apart of the open ends of the side branches 8 and 9, has been increased by stretching the interior sides 23 of the central bellows 13 and 14.

It is also possible to lengthen or shorten the side branches 8 and 9 according to arrows "c". This is carried out by stretching or by compressing the side bellows respectively 15 and 16. An impression tray with stretched side branches 8 and 9 is represented by FIG. 8.

By combining these various elementary adjustments, it is possible to obtain any kind of shape or variation. The impression tray according to the invention thus advantageously provides a perfect match and adaptation to be achieved for all dental anatomical forms encountered.

In the same way, the impression tray sections 19, obtained after rupture of the split lines 17 and 18, can also be adjusted as represented on FIG. 9.

The two central bellows 13 and 14 of the section of the impression tray 20 make it possible in this embodiment to undergo the three elementary adjustments "a", "b" and "c" previously described.

The impression tray side sections 21 and 22 can be lengthened or shortened according to arrows "c". This is carried out while stretching or by compressing their respective bellows 15 or 16.

One can consider many other alternatives of the preceding embodiments without deviating from the scope of the invention.

Thus for example, the sidewalls 4, 5 and 105 were represented with a longitudinal end at right angle to the base 3. However, one can imagine that this embodiment could comprise of several ergonomic end profiles or round-offs. These make it possible to correspond better to the anatomical shape of the patient. In the same way, gutters 2 and 102 can have a form or a curve slightly different from those represented.

Means of reinforcement and strengthening can additionally be envisaged in the region of bellows 12. These make it possible to maintain the shape and to strengthen the impression tray in the configuration desired after adjustment. They thus make it possible to avoid any risk of movement or distortion or other change during the capture of the impression.

Figure 10:
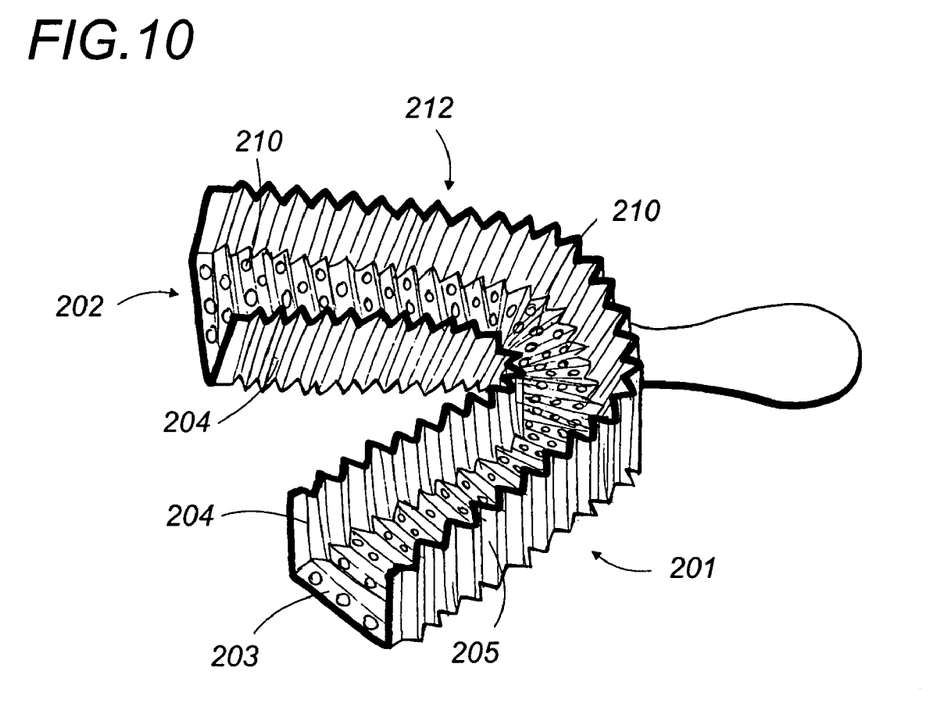
FIG. 10 is a perspective top view of another alternative impression tray according to the invention for inferior dental arch, comprising a single concertina cover extending over the entire length from the gutter.

As represented on FIG. 10, an impression tray 201 can also be considered for example in the shape of a single bellow 212, preferably in the aforementioned accordion style. This bellow extends over the entire length of the gutter 202.

This alternative has the advantage of providing a single type of surface. There is no alteration of smooth and folded surfaces, which considerably facilitates its manufacture. Moreover, it offers unequalled possibilities of adjustment, while remaining very simple for fast and practical use.

Figure 11:
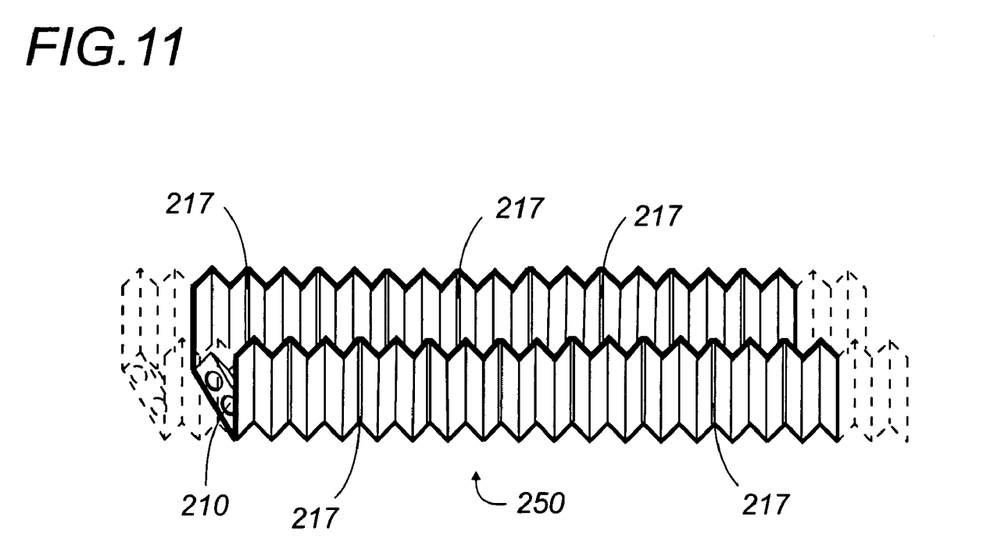
FIG. 11 is a perspective view for a section for important length to concertina cover, sectionnable at the time of the use, making it possible to carry out the alternative of the impression tray according to the invention shown on FIG. 10.

This alternative can be easily achieved by a long section 250 as represented in FIG. 11, this long length being intended to be shortened by division to a suitable length appropriate for the particular use at the time of application.

On this section, transverse split lines 217 can be envisaged at regular intervals, these split lines being similar to those already described.

One can, in addition, imagine zones more deformable than others. These are localized at the places envisaged in the initial version to facilitate the adaptation to the desired form.

Of course, perforations 210 can cross base 203 and/or the sidewalls, interior 204 and external 205, of the impression tray. These perforations allow the evacuation and the adhesion of the paste during capture of the impression.

In order to maintain stability of the final form after adjustment, it may be necessary to utilize additional stiffeners, for example non-deformable clips or blades or other interior reinforcement capable of permanent deformation i.e. deformable without elastic recovery effect.

In the continuation of this description the following describes some examples of the means of strengthening that may be required during use of the impression tray according to the invention.

The transverse and longitudinal rigidity of the impression tray according to the invention is achieved by a series of rigid sections and sections with bellows and by the use of an appropriate material of construction.

One will thus carry out an optimal series of these sections. The sequence and the length of each one of them are a function of the application and the required particular effect.

It should be remembered that the internal surfaces of the impression tray could be covered with an adhesive layer.

However, there are new materials that can harden with heat, and also harden with specific light and in particular with ultraviolet or infrared radiation. One can thus plan to construct the impression tray by adapting it in length and width to match the specific application and to then immobilize it or to fix it rigidly in this altered form for later use on the patient.

An additional improvement with rigidity can come from one or several elements of strengthening and in particular from longitudinal reinforcements, basic reinforcements and possibly of transverse reinforcements.

Figure 12:
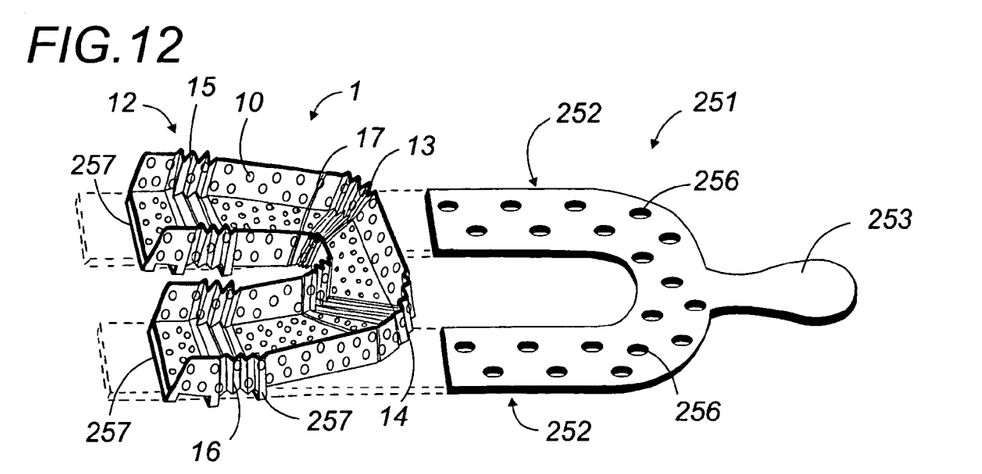
FIG. 12 is a perspective view of an impression tray for the inferior dental arch according to the alternative of FIG. 1, and a plate-support for rigidification.
Figure 13:
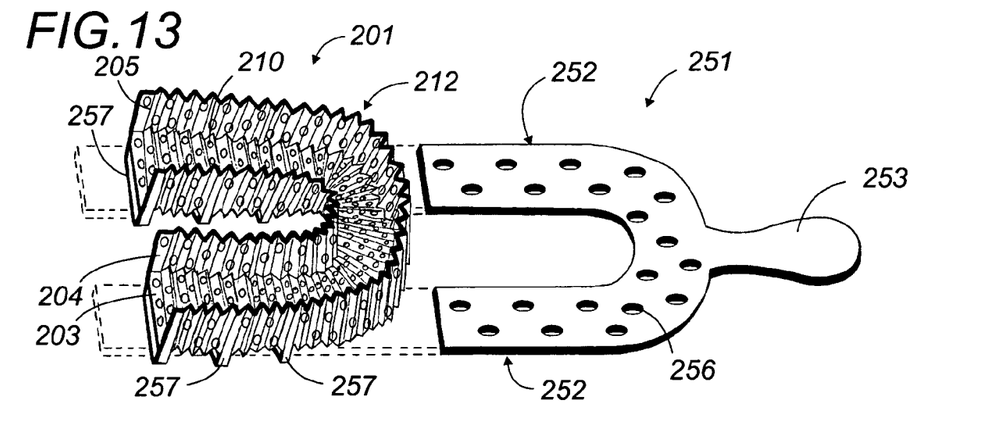
FIG. 13 is a perspective view of an impression tray for lower dental arch according to the alternative of FIG. 10, accompanied by a plate-support for rigidification.

A particular alternative is represented by FIGS. 12 and 13. In these Figures, the two principal alternatives that have been detailed above are supported on their bottom face by a plate-support 251. This plate-support 251 is preferably in the general shape of a "U" lying down with two branches 252. This plate-support also comprises an end strip handle 253. This reinforcing plate 251 is flat and a minimum flexible. Branches 252 are thus flexible enough to be able to deviate slightly and thus adapt over a certain dimensional range.

Figure 14:
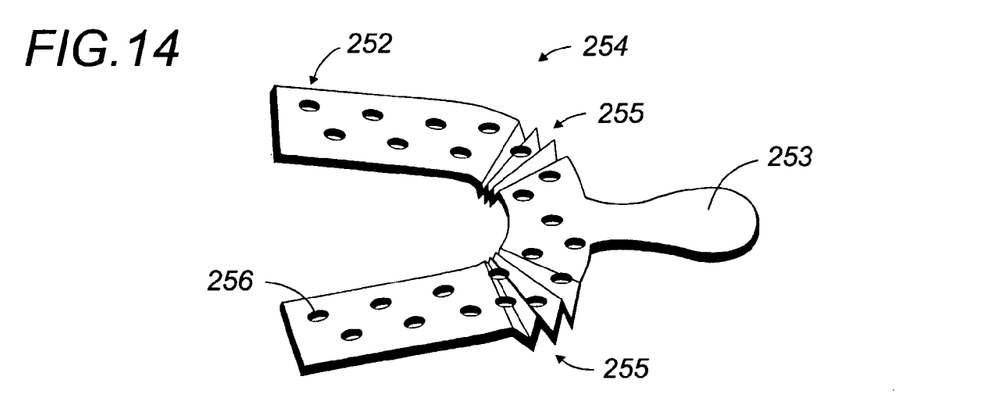
FIG. 14 is a perspective top view of a plate-support of adjustable rigidification able to equip an impression tray according to the invention.

This element of strengthening is used as a plate at the time of capturing the impression. It can be specific to a given model or cover several models until a certain dimensional variation is encountered beyond which this profile will need to be replaced by a larger or smaller profile. This element of strengthening can also be accomplished by using an adaptable plate-support 254 shown in one configuration in FIG. 14. This plate-support comprises means of adjustment 255. In the case represented, only the spacing of the branches is adjustable, for example by sections made out of mini or micro bellows 255 as represented in FIG. 14.

Just like the impression tray, the fixed plate-support 251 or adjustable plate-support 254 can be provided with openings 256 making it possible for any excess or surplus paste material to escape during capture the impression.

Figure 17:
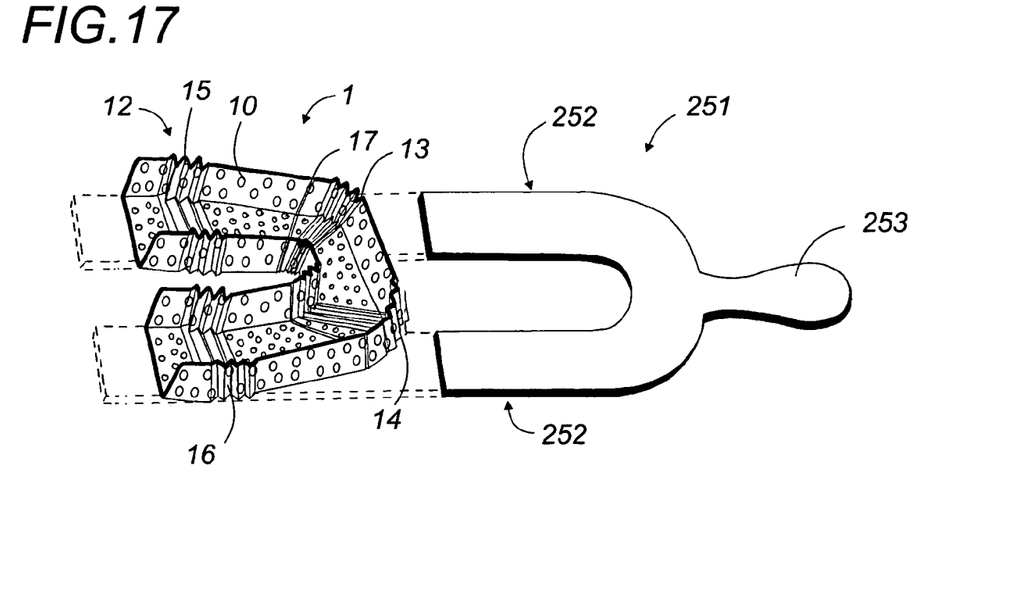
FIG. 17 is a perspective view of the alternative of FIG. 12 impression tray with a plate-support for rigidification to be stuck.

This fixed plate-support 251 or adjustable plate-support 254 perforated or not can be bonded for example with the external face of the base wall of the impression tray before its use using adhesives compatible with the application for example adhesives of the food type (FIG. 17).

More generally, any element of strengthening can be bonded using adhesives compatible with the application for example adhesives of the food type.

So that the base reinforcement remains in contact with the bottom and in the correct place, one will be able to envisage, the means required. They are bridges 257 in the form of "U" shaped loops or other similar equivalents placed in undercuts in the body of the impression tray or externally in a local depression in the base.

This embodiment also makes it possible to carry out in a simple way a double impression tray adapted to the patient (not represented). It is simply a matter of superimposing two impression trays of this type and joining them together or assembling them using the simple "U" shaped loops 257 and introducing the branches 252 of the plate-support 251 or 254 between two impression trays. Each branch 252 ensures the connection or assembly of the two impression trays superimposed. One will thus be able, at the same time and without additional significant cost, to take an impression of the lower and upper jaw.

Other alternatives are possible in particular those with a receiving shape in the form of a double tray.

Figure 15:
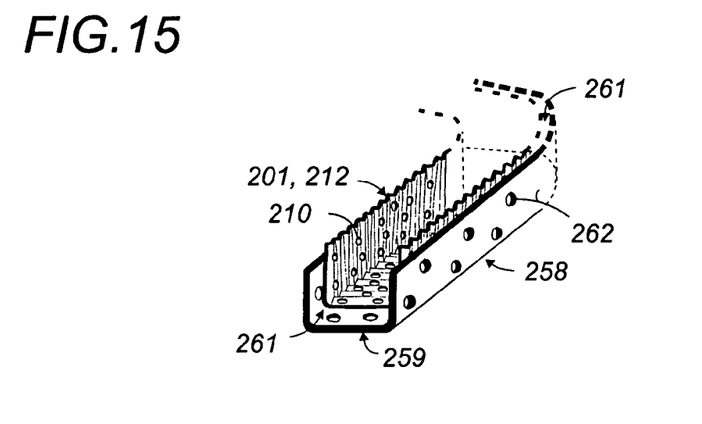
FIG. 15 is a perspective view of a section of the impression tray according to the invention placed in a receiving gutter for rigidification.
Figure 16:
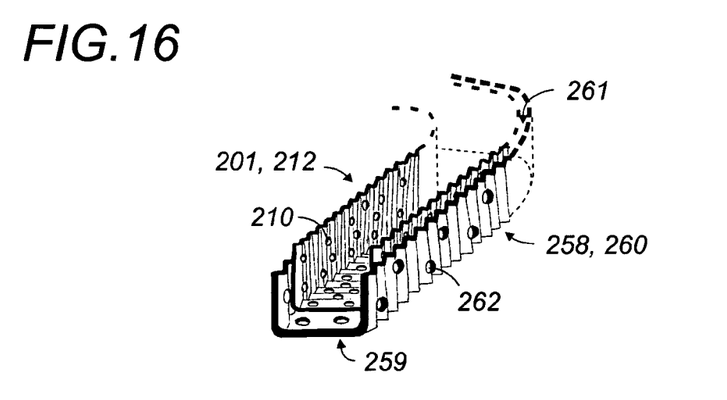
FIG. 16 is a perspective view of a section of the impression tray according to the invention placed in a receiving deformable rigidification gutter.

According to these alternatives, one can provide a receiving form 258 broader than the impression tray, for example in the shape of gutter 259 as represented on FIGS. 15 and 16.

It can comprise means of adjustment, for example of the same type as the impression tray. These means of adjustment are deformable according to the same principle. It is for example the case of the gutter with bellows 260 of FIG. 16.

The additional width makes it possible to gain an intermediate space 261 of narrow width. This space 261 will enable the residual enclosed air and paste material driven out by the volume of the teeth to escape through the openings 210.

The receiving profile gutter 259 can also be provided with openings 262, preferably on all its faces. This will allow the impression paste material used to capture the impression to be driven out at the time the impression is made. Projections or reliefs towards the outside (not represented) will maintain the shape automatically. Many methods or wider local spacers can be used to construct these projections or reliefs. To this end, and for example, the projections of the "U" shaped loops 257 can constitute these spacers.

Still other alternatives are possible within the scope of this invention.

One can imagine for example embodiments for which one uses heating flat-nose pliers. These heating flat-nose pliers are intended to strengthen certain zones locally in particular those corresponding to the site of the prosthesis.

However, it must be well understood that even if certain preferential alternatives of the device according to the invention were more particularly described and represented, they constitute only further examples of achievement, the scope of the invention being defined by the appended claims.

The invention claimed is:

1. An impression tray for capture of one or more of a sectoral or total impression of one or more of an upper jaw or a lower jaw, the impression tray comprising:
    a gutter (2, 102, 202) in a general shape of an arch with a central curved section (7, 107) extending on first and second sides by two side branches (8, 9, 108, 109), the gutter comprising;
        a bottom wall (3, 103, 203) bordered longitudinally by an interior side wall (4, 104, 204) and an external side wall (5, 105, 205), and thus defining a receiving throat (6, 106) being able to be filled with an impression paste; and
        at least an integrated deformable zone, deformable at a temperature of use and having a multidirectional extension portion (12, 112, 212) extending contiguously across the entire bottom wall, interior side wall and external side wall of the gutter to facilitate both angular adjustment and a change of length of the gutter.

2. The impression tray according to claim 1, wherein the multidirectional extension portion includes an extendable structure (13 to 16, 113 to 116, 212).

3. The impression tray according to claim 2, wherein the extendable structure is a bellow (13 to 16, 113 to 116, 212).

4. The impression tray according to claim 1, wherein the impression tray further comprises a first, second, third and fourth multidirectional extensions (13 to 16, 113 to 116).

5. The impression tray according to claim 4, wherein the first and second multidirectional extension (13, 14, 113, 114) are located on the central curved section (7, 107) of the gutter (2, 102) and the third and fourth multidirectional extension (15, 115, 16, 116) are provided on each of the side branches (8, 108, 9, 109) of the gutter.

6. The impression tray according to claim 1, wherein the impression tray has perforations (10, 110, 210).

7. The impression tray according to claim 1, wherein the impression tray further comprises a gripping stem (11, 111).

8. The impression tray according to claim 1, wherein the impression tray is in a shape of a single bellow (212) extending along an entire length of the gutter (202).

9. The impression tray according to claim 8, wherein the impression tray has separatable sections (250), intended to be divided upon use.

10. The impression tray according to claim 9, wherein the interior side wall (104) of the gutter (102) widens and joined partly higher by forming a vault, in order to match with a shape of a roof of a mouth, thus making it possible to capture the impression of a velum in addition to that of the higher dental arch.

11. The impression tray according to claim 10, wherein the means of extension (113 to 116) are prolonged on the interior side vault (104), allowing an adjustment of the impression tray (101) in a vault (104) region.

12. The impression tray according to claim 1, wherein impression tray has at least a split zone (17, 18, 217) of lower mechanical resistance, allowing the impression tray to split into one or more impression tray sections (19).

13. The impression tray according to claim 12, wherein the one or more impression tray sections (19) obtained by rupture of the at least a split zone (17, 18, 217) of the impression tray comprise at least an integrated deformable zone deformable at temperature of use in the form of a means of multidirectional extension (12, 112, 212).

14. The impression tray according to claim 1, wherein the impression tray further comprises a rigid element (251, 254, 259, 260) having one or more of constant length or adjustment means.

15. The impression tray according to claim 14, wherein the rigid element is a plate-support (251, 254).

16. The impression tray according to claim 15 wherein the plate-support (251, 254) is in a general shape of a U laid down with two branches (252) and having an end forming a strip-handle (253).

17. The impression tray according to claim 15 wherein the impression tray further comprises bridges (257) of material of a type of pass-girdles.

18. The impression tray according to claim 16, wherein the element of rigidification is a receiving form (258) broader than the impression tray.

19. The impression tray according to claim 18 wherein the receiving form (258) is in a shape of the gutter (259).

20. The impression tray according to claim 19, wherein a distance between the interior and the exterior side walls of the impression tray and the sides of the receiving form is maintained constant by spacers.

21. An impression tray for capture of one or more of a sectoral or total impression of one or more of an upper jaw or a lower jaw, the impression tray comprising:
- a gutter (2, 102, 202) in a general shape of an arch with a central curved section (7, 107) extending on first and second sides by two side branches (8, 9, 108, 109), the gutter comprising;
- a bottom wall (3, 103, 203) bordered longitudinally by an interior side wall (4, 104, 204) and an external side wall (5, 105, 205), and thus defining a receiving throat (6, 106) being able to be filled with an impression paste;
- an interior edge of the gutter formed on the interior side wall, and an external edge of the gutter formed on the external side wall; and
- at least an integrated deformable zone formed in the gutter, said deformable zone comprising a contiguous bellows extending from said interior edge completely across the interior wall, the bottom wall and the external wall to the external edge of the gutter to define a multidirectional extension portion (12, 112, 212) which permits both angular alignment and lengthwise extension of the gutter.

* * * * *